(12) United States Patent
Zheng et al.

(10) Patent No.: US 11,492,606 B2
(45) Date of Patent: Nov. 8, 2022

(54) NITRILASE MUTANT, CONSTRUCTION METHOD THEREFOR, AND APPLICATION THEREOF

(71) Applicant: ZHEJIANG UNIVERSITY OF TECHNOLOGY, Hangzhou (CN)

(72) Inventors: Renchao Zheng, Hangzhou (CN); Yuguo Zheng, Hangzhou (CN); Qin Zhang, Hangzhou (CN); Zheming Wu, Hangzhou (CN); Xiaoling Tang, Hangzhou (CN); Xiafeng Lu, Hangzhou (CN)

(73) Assignee: ZHEJIANG UNIVERSITY OF TECHNOLOGY, Hangzhou (CN)

( * ) Notice: Subject to any disclaimer, the term of this patent is extended or adjusted under 35 U.S.C. 154(b) by 19 days.

(21) Appl. No.: 16/968,808

(22) PCT Filed: Jan. 31, 2019

(86) PCT No.: PCT/CN2019/074110
§ 371 (c)(1),
(2) Date: Aug. 10, 2020

(87) PCT Pub. No.: WO2019/154249
PCT Pub. Date: Aug. 15, 2019

(65) Prior Publication Data
US 2021/0009981 A1 Jan. 14, 2021

(30) Foreign Application Priority Data
Feb. 9, 2018 (CN) .......................... 201810136409.4

(51) Int. Cl.
*C12N 9/78* (2006.01)
*C12P 13/00* (2006.01)
*C12N 15/70* (2006.01)

(52) U.S. Cl.
CPC ............... *C12N 9/78* (2013.01); *C12N 15/70* (2013.01); *C12P 13/002* (2013.01); *C12Y 305/05001* (2013.01)

(58) Field of Classification Search
CPC .................................. C12N 9/78; C12P 13/002
See application file for complete search history.

(56) References Cited

U.S. PATENT DOCUMENTS 7,361,507 B1 * 4/2008 Pierrard ................... C12N 9/78
435/18

FOREIGN PATENT DOCUMENTS

| CN | 104962540 | 10/2015 |
| CN | 105176955 | 10/2015 |

OTHER PUBLICATIONS

Xie, Zhiyi et al. "Cloning and Optimization of a Nitrilase for the Syntheisis of (3S)-3-Cyano-5-Methyl hexanoic Acid", Journal of Molecular Catalysis B: Enzymatic, vol. 41, Jun. 5, 2006, pp. 75-80.

* cited by examiner

*Primary Examiner* — Yong D Pak
(74) *Attorney, Agent, or Firm* — Jiwen Chen

(57) ABSTRACT

The present invention discloses a nitrilase mutant and its construction method and its application in the synthesis of chiral intermediate of pregabalin in the technical field of bioengineering. The present invention, respectively, takes turnip nitrilase BrNIT and arabidopsis nitrilase AtNIT as parent, using peptide fragment displacement method, displaces the sites 226-286 of BrNIT amino acid sequence and sites 225-285 of AtNIT amino acid sequence with sites 225-285 of *Arabis alpina* L. nitrilase AaNIT, obtain nitrilase mutants $BrNIT_{225-285}$ and $AtNIT_{225-285}$ of which the amino acid sequence is as shown in SEQ ID NO.1 or SEQ ID NO.3. Compared with wild type nitrilase, the activity of the nitrilase mutant provided by the present invention in catalyzing and hydrolyzing racemic IBSN and the stereoselectivity of the product show substantial improvement, it can satisfy the requirements of industrial application, and has good application prospect in efficient catalysis of racemic IBSN to synthesize 3-cyano-5-methylhexanoic Acid.

9 Claims, 2 Drawing Sheets
Specification includes a Sequence Listing.

NITRILASE MUTANT, CONSTRUCTION METHOD THEREFOR, AND APPLICATION THEREOF

This is a U.S. national stage application of PCT Application No. PCT/CN2019/074110 under 35 U.S.C. 371, filed Jan. 31, 2019 in Chinese, claiming priority of Chinese Application No. 201810136409.4, filed Feb. 9, 2018, all of which are hereby incorporated by reference.

TECHNICAL FIELD

The present invention relates to the technical field of biological engineering, specifically relates to a nitrilase mutant with improved catalytic activity and stereoselectivity and its application in the synthesis of chiral intermediate of pregabalin.

BACKGROUND ART

Nitrilase (Nitrilase EC 3.5.5.1) is a biocatalyst that catalyzes the hydrolysis of nitrile compound (R-CN) to produce carboxylic acid and ammonia, which is widely applied in the synthesis of (chiral) amino acid, carboxylic acid and their derivatives. Enzymatic hydrolysis of nitrile is appreciated in the academic circle and the industrial circle due to its advantages of mild reaction conditions, efficient process, friendly environment and high chemoselectivity, regio selectivity and stereo selectivity, etc.

Due to that wild-type nitrilase is generally difficult to adapt to the demands of industrial environment, improving the catalytic performance of nitrilase by means of rational and non-rational protein modifications has become a research hotspot. DeSantis et al use point saturation mutation technology to modify wild-type nitrilase, and the obtained mutant A190H is able to catalyze 3 M 3-hydroxyglutaronitrile to produce (R)-4-cyano-3-hydroxybutyrate with the product ee value of up to 99% (J. Am. Chem. Soc., 2003,125:11476-11477). Schreiner et al utilize PCR technology to modify nitrilase AtNIT2 from *Arabidopsis thaliana*, and the activity of the obtained nitrilase towards benzyl cyanide hydrolysis is improved by 4 times (ChemCatChem, 2010, 2:263-267).

Pregabalin, of which the chemical name is (3S)-3-aminomethyl-5-methylhexanoic acid, is a first-line drug that treats neuropathic pain, epilepsy, anxiety and nervous centralis pain caused by spinal cord injury, trauma or multiple sclerosis etc. Compared with traditional drugs of the similar type, pregabalin has the advantages of low dose, low administration times, long duration, less side effect and high tolerance etc., which has become one of the best-selling drugs in the world.

Construction of the chiral center is the key to pregabalin synthesis, research on synthesis of pregabalin chiral intermediate through biocatalysis is getting more and more attention. Nitrilase-mediated hydrolysis of isobutylsuccinonitrile (IBSN) is a highly attractive approach for (S)-3-cyano-5-methylhexanoic acid ((S)-CMHA), the critical chiral intermediate of pregabalin. However, the catalytic activity of the nitrilase in the prior art is low (J. Mol. Catal. B: Enzym. 2006, 41:75-80), and is difficult to satisfy the requirement of industrial application. Therefore, developing nitrilase mutant construction technology and obtaining nitrilase of high activity plays an important role for efficient manufacturing of pregabalin.

SUMMARY OF THE INVENTION

The purpose of the present invention is to modify wild-type nitrilase by means of genetic engineering, in a bid to achieve significant improvement of catalytic performance of the modified nitrilase such as catalytic activity and stereoselectivity and meet the requirements of industrial application.

In order to realize such objects, the technical solution as follows is adopted in the present invention:

A nitrilase mutant, of which the amino acid sequence is as shown in SEQ ID NO.1 or SEQ ID NO.3.

In the present invention, the amino acid sequences of crucifer turnip (*Brassica rapa*) nitrilase (BrNIT) and (*Arabidopsis thaliana*) arabidopsis nitrilase (AtNIT) are respectively displaced, especially the multiple sites of amino acid in the area of sites 225-285 are displaced to obtain the nitrilase mutant as shown in SEQ ID NO.1 or SEQ ID NO.3. Research proved that compared with wild-type nitrilase, the catalytic activity and stereoselectivity of the mutant to the substrate racemic IBSN were significantly improved.

Conservative substitutions of other amino acid sites of the nitrilase, addition or deletion of one or a few amino acids, N-terminal truncations and C-terminal truncations, such mutant forms also fall in the scope of the present invention.

The present invention further provides a coding gene that encodes the nitrilase mutant, of which the nucleotide sequence is as shown in SEQ ID NO.2 or SEQ ID NO.4.

The present invention further provides a recombinant vector containing the coding gene. Preferably, the original vector is pET28b.

The present invention further provides a recombinant strain containing the recombinant vector. The recombinant vector is introduced into the host cell to obtain the recombinant genetic engineering strain. The host cell can be various normal host cells in this field. Preferably, the host cell is *Escherichia coli* BL21.

Another object of the present invention is to provide a method for preparing the nitrilase mutant, comprising the steps as follow:

(1) based on turnip nitrilase gene or arabidopsis nitrilase gene sequence, designing PCR primer. Using *Arabis alpina L.* cDNA as a template, utilizing the primer for amplification to obtain DNA fragment I or DNA fragment II that contains sites 673-855 of the *Arabis alpina L.* nitrilase nucleotide sequence;

(2) taking the recombinant plasmid that carries turnip nitrilase gene or arabidopsis nitrilase gene sequence as a template, utilizing reverse PCR amplification to obtain the BrNIT plasmid fragment lack in sites 676-858 of turnip nitrilase nucleotide sequence or obtain the AtNIT plasmid fragment lack in sites 673-855 of arabidopsis nitrilase nucleotide sequence;

(3) recombining DNA fragment I with BrNIT plasmid fragment or recombining DNA fragment II with AtNIT plasmid fragment, and introducing the recombinant product into the host bacteria to obtain a nitrilase mutant expression strain;

(4) conducting induced expression of the nitrilase mutant strain to obtain the nitrilase mutant.

Crucifer turnip (*Brassica rapa*) nitrilase (BrNIT), arabidopsis (*Arabidopsis thaliana*) nitrilase (AtNIT) and *Arabis alpina L.* (*Arabis alpine*) nitrilase (AaNIT) all have the activity of catalyzing racemic IBSN to produce pregabalin chiral intermediate (S)-3-cyano-5-methylhexanoic acid. However, they have different advantages and disadvantages in terms of catalytic activity and stereoselectivity. In the present invention, the turnip nitrilase BrNIT and arabidopsis nitrilase AtNIT was taken as parents and using peptide fragment displacement method, the 226-286 peptide fragment of BrNIT amino acid sequence and 225-285 peptide fragment of AtNIT amino acid sequence were replaced with 225-285 peptide fragment of *Arabis alpina* L. nitrilase AaNIT, to obtain nitrilase mutants BrNIT$_{225-285}$ and AtNIT$_{225-285}$, respectively, of which the amino acid sequence is as shown in SEQ ID NO.1 or SEQ ID NO.3, in a bid to improve the catalytic activity and stereoselectivity of nitrilase.

The preferred plasmid in step (2) is pET28b.

The preferred PCR primer required for preparing nitrilase mutant BrNIT225-285 in step (1) for amplifying DNA fragment I is:

```
Forward primer:
                                    (SEQ ID NO: 22)
5'-GAATGGCAGTCTTCTATGATGCACATCGC-3';

Reverse primer:
                                    (SEQ ID NO: 24)
5'-GAAGTTCGGACCAGCCAGAACCTGACCC-3'.
```

The preferred PCR primer required for amplifying BrNIT plasmid fragment in step (2) is:

```
Forward primer:
                                    (SEQ ID NO: 25)
5'-GCGATGTGCATCATAGAAGACTGCCATTC-3';

Reverse primer:
                                    (SEQ ID NO: 26)
5'-GGGTCAGGTTCTGGCTGGTCCGAACTTC-3'.
```

The preferred PCR primer required for preparing nitrilase mutant AtNIT225-285 in step (1) for amplifying DNA fragment II is:

```
Forward primer:
                                    (SEQ ID NO: 31)
5'-CTAAAGAATGGCAGTCTTCTATGCTGCACATCGC-3';

Reverse primer:
                                    (SEQ ID NO: 32)
5'-GATTCGAAGTTCGGACCAGCCAGAACCTGACCCAGC-3'.
```

The preferred PCR primer required for amplifying AtNIT plasmid fragment in step (2) is:

```
Forward primer:
                                    (SEQ ID NO: 33)
5'-GCGATGTGCAGCATAGAAGACTGCCATTCTTTAG-3';

Reverse primer:
                                    (SEQ ID NO: 34)
5'-GCTGGGTCAGGTTCTGGCTGGTCCGAACTTCGAATC-3'.
```

Preferably, the host cell is Escherichia coli BL21.

Another object of the present invention is to apply the nitrilase mutant in catalyzing racemic IBSN to prepare (S)-3-cyano-5-methylhexanoic acid.

Specifically, the recombinant strains containing nitrilase mutant coding genes were taken as biocatalyst in the formation of immobilized wet cell, wet cell or the purified enzyme extracted from ultrasonication of the wet cell. Racemic IBSN is used as a substrate, the reaction medium is used as buffer solution with pH 5.0-10.0, and the reaction is performed at 25-45° C. and 100-300 rpm. After the reaction is completed, the reaction mixture containing (S)-3-cyano-5-methylhexanoic acid is obtained, which was further separated and purified.

Preferably, in the reaction system, the final concentration of the substrate is 0.5-1.5 M, the used wet cell content is 10-30 g/L. Further preferably, the additive amount of the wet cells required for conversion of 1 mol substrate is 20 g.

Preferably, the reaction medium is Tris-HCl buffer solution with pH 8.0.

Preferably, the hydrolysis reaction is conducted at 30-35° C., 200 rpm.

Preferably, the applied wet cell is recombinant *Escherichia coli* BL21(DE3)/pET28b-BrNIT$_{225-285}$ or *E. coli* BL21 (DE3)/pET28b-AtNIT$_{225-285}$ containing nitrilase mutant coding gene. The fermentation culture is as follows: the recombinant *Escherichia coli* containing nitrilase mutant coding gene is inoculated in LB culture medium containing kanamycin and cultured until OD$_{600}$ reaches 0.6-0.8, after which isopropyl-β-D-thiogalactopyranoside (IPTG) with a final concentration of 0.1 mM is added to induce the protein expression at 28° C. for 10-12 hours. After centrifugation, the cells were collected.

Compared with the previous invention, the present invention has the following benefits:

(1) The present invention provides a directed enzyme modification method, which displaces the critical peptide fragment of the turnip nitrilase or arabidopsis nitrilase with the critical peptide fragment of *Arabis alpina* L. nitrilase, to construct nitrilase mutant with improved activity and stereoselectivity, which has good application prospect in efficient catalyzing racemic IBSN to synthesize (S)-3-cyano-5-methylhexanoic acid.

(2) The activity of the nitrilase mutant BrNIT$_{225-285}$ catalyzing the hydrolysis of racemic IBSN is 2.5 times of that of wild type and the enantiomeric ratio (E value) is increased from 200 to 500 or above; while the activity of AtNIT$_{225-285}$ catalyzing racemic hydrolysis of IBSN is 1.9 times of that of wild type. The stereoselectivity is improved without compromising catalytic activity, which satisfies the requirement of industrial application.

DETAILED DESCRIPTION OF THE EMBODIMENTS

Figure 1:
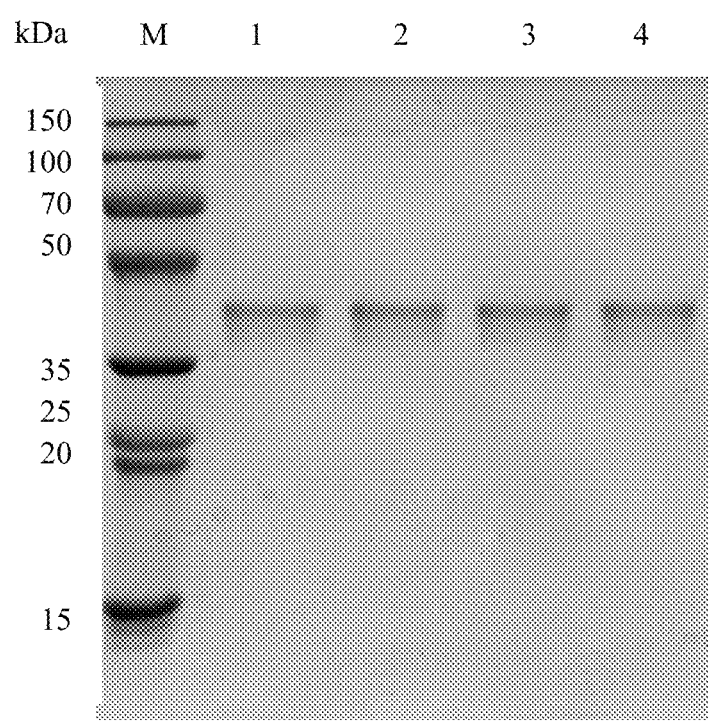
FIG. 1 is SDS-PAGE of nitrilase and its mutants after protein purification. Lane 1 is BrNIT, lane 2 is BrNIT$_{225-285}$, and lane 3 is AtNIT, lane 4 is AtNIT$_{225-285}$.

Below is further description of the invention in conjunction with embodiments, however, the scope of protection of the present invention is not limited to these embodiments only.

The sources of the main experimental materials of the following embodiments:

*Escherichia coli* host strains *E. coli* BL21(DE3) and *E. coli* BL21(DH5α) were purchased from Transgen; the expression vector pET-28b(+) was purchased from Novagen; Phanta Max Super-Fidelity DNA Polymerase was purchased from Vazyme; 2xTsingKe Master Mix(blue) were purchased from TsingKe; kanamycin was purchased from Takara Bio (Dalian); IPTG is product of Promega.

Embodiment 1

1. Construction of Nitrilase Mutants

The present invention adopts a simple, quick and efficient seamless DNA cloning technology (ClonExpress®) to conduct directed cloning of the amplified peptide fragment into the BrNIT plasmid fragment that is missing the corresponding gene segment.

Through comparing and analyzing the nucleotide sequence and amino acid sequence of crucifer nitrilase, the peptide fragments were determined. The amino acid sequence of the wild type turnip nitrilase was SEQ ID No.5, this protein was coded by the nucleotide sequence of SEQ ID No.6; the amino acid sequence of the wild type Arabis alpina L. nitrilase was SEQ ID No.7, this protein was coded by the nucleotide sequence of SEQ ID No.8.

The AaNIT nucleotide sequence was taken as template for cloning peptide fragment sites 0-85, 85-175, 175-225, 225-285 and 285-342, respectively.

Meanwhile, the recombinant plasmid containing BrNIT nucleotide sequence was taken as a template and the corresponding primers were designed to amplify the BrNIT plasmid fragment that is missing 0-86, 86-176, 176-226, 226-286 and 286-342 peptide fragment.

The plasmid containing BrNIT sequence that is missing the corresponding peptide fragment was linearized, and the forward/reverse PCR primer 5' for amplifying the inserting fragment was introduced with the terminal sequence of the linearized plasmid, allowing the terminals of PCR primers 5' and 3' respectively bear sequences consistent to the two terminals of the linearized vector. The primer sequences were as shown in Table 1.

The PCR amplification for the peptide fragments was conducted as follows: PCR reaction system (50 μL): Template DNA<1 μg, 2×TsingKe® Master Mix, forward and reverse primers at 0.2 μM respectively, ddH$_2$O was supplemented to the total volume. The PCR progress was performed at 94° C. for 5 minutes, followed by 30 cycles of 94° C. for 30 seconds, 58° C. for 30 seconds and 72° C. for 10 seconds, after which, the reaction was performed at 72° C. again for 10 minutes. The amplified products went through agarose gel electrophoresis analysis, excising recovery, inactivated at 65° C. for 10 minutes, and placed at 4° C. for use.

Vector linearization was achieved through reverse PCR amplification. PCR reaction system (50 μL) was as follows: template DNA 0.1 ng-1 ng, 2×Phanta Max Buffer, dNTPs (10 mM each) 0.2 mM, forward and reverse primers at 0.2 μM respectively, Phanta Max Super-Fidelity DNA Polymerase 1 U, ddH$_2$O was supplemented to the total volume. The PCR progress was performed at 95° C. for 30 seconds, followed with 30 cycles of 95° C. for 15 seconds, 63° C. for 15 seconds and 72° C. for 6.0 minutes, after which the reaction was performed at 72° C. for 5 minutes. The amplified products went through agarose gel electrophoresis analysis, excising recovery, inactivated at 65° C. for 10 minutes, and placed at 4° C. for use.

TABLE 1

BrNIT chimeric enzyme primer design table

| Primer designation | Primer sequence (5' to 3') |
|---|---|
| Peptide fragments (0-85) forward primer | CCATGTCTGGTAAAGAAGAAATGTC (SEQ ID NO: 11) |
| Peptide fragments (0-85) reverse primer | CGTTGTGAACACCAACACCTATACCG (SEQ ID NO: 12) |
| Cloning vectors (0-86) forward primer | GACATTTCTTCTTTACCAGACATGGTATATCTCC (SEQ ID NO: 13) |
| Cloning vectors (0-86) reverse primer | CGGTATAGGTGTTGGTGTTCACAACG (SEQ ID NO: 14) |
| Peptide fragments (85-175) forward primer | GTGTAGGTGTGCACAACGAAGACGGTCGTGACGAATTC (SEQ ID NO: 15) |
| Peptide fragments (85-175) reverse primer | GTCGAACCGTCACCGTAACCCCAGATGCAACGTTCCAG (SEQ ID NO: 16) |
| Cloning vectors (86-176) forward primer | GAATTCGTCACGACCGTCTTCGTTGTGCACACCTACAC (SEQ ID NO: 17) |
| Cloning vectors (86-176) reverse primer | CTGGAACGTTGCATCTGGGGTTACGGTGACGGTTCGAC (SEQ ID NO: 18) |
| Peptide fragments (175-225) forward primer | GGTGACGGTTCGACTATCCCGGTGTACGAC (SEQ ID NO: 19) |
| Peptide fragments (175-225) reverse primer | GCGATGTGCAGCATAGAAGACTGCCATTC (SEQ ID NO: 20) |
| Cloning vectors (176-226) forward primer | GTCGTACACCGGGATAGTCGAACCGTCACC (SEQ ID NO: 21) |
| Cloning vectors (176-226) reverse primer | GAATGGCAGTCTTCTATGCTGCACATCGC (SEQ ID NO: 22) |
| Peptide fragments (225-285) forward primer | GAATGGCAGTCTTCTATGATGCACATCGC (SEQ ID NO: 23) |
| Peptide fragments (225-285) reverse primer | GAAGTTCGGACCAGCCAGAACCTGACCC (SEQ ID NO: 24) |
| Cloning vectors (226-286) forward primer | GCGATGTGCATCATAGAAGACTGCCATTC (SEQ ID NO: 25) |
| Cloning vectors (226-286) reverse primer | GGGTCAGGTTCTGGCTGGTCCGAACTTC (SEQ ID NO: 26) |
| Peptide fragments (285-342) forward primer | GGTAAAATCCTGGCGGGTCCGAACTTCGAATC (SEQ ID NO: 27) |
| Peptide fragments (285-342) reverse primer | GTGGTGGTGGTGGTGCTCGAGTCTTTTTTTCGG (SEQ ID NO: 28) |
| Cloning vectors (286-343) forward primer | GATTCGAAGTTCGGACCCGCCAGGATTTTACC (SEQ ID NO: 29) |
| Cloning vectors (286-343) reverse primer | CCGAAAAAAAGACTCGAGCACCACCACCAC (SEQ ID NO: 30) |

NanoDrop™ One/OneC ultramicro-UV spectrophotometer was used to calculate the concentration of the above obtained insert fragments and linearized vectors. The additive amounts of the linearized vectors were calculated for the insert peptide fragments and the corresponding missing peptide fragments. Composition of the ligation reaction system was shown in Table 2. The PCR sample was mixed and placed at 37° C. for 30 minutes, then reduced to 4° C.

TABLE 2 recombination reaction system

| Component | Recombination reaction |
|---|---|
| Linearized vector | 0.03 pmol |
| Insert fragment | 0.06 pmol |
| 5 × CE II Buffer | 4 µL |
| Exnase II | 2 µL |
| ddH$_2$O | to 20 µL |

10 µL recombinant product was added into 100 µL E. coli BL21(DH 5α) competent cell, which was sprayed onto LB plate with 50 mg/L kanamycin. The plates were cultured at 37° C. for 10-12 h. A single colony was picked into LB fluid medium with 50 mg/L kanamycin for plasmid extraction. The positive colonies were transformed into E. coli BL21 (DE3) competent cell and cultured overnight to obtain nitrilase mutant expression strain.

2. Nitrilase Mutant Gene Expression

A single colony was picked and placed into 5 mL LB fluid medium with kanamycin at a final concentration of 50 mg/L. The cultivation was performed at 37° C. and 200 rpm for 6-8 hours. The above seed solution was transferred to fresh LB fluid medium containing 50 mg/L kanamycin at 2% volume ratio, which was also cultured at 37° C. and 150 rpm. Until the OD$_{600}$ of the cell culture reached about 0.6-0.8, IPTG (final concentration at 0.1 mM) was added to induce the gene expression at 28° C. and 150 rpm for 10-12 hours. The cultured cells were collected and centrifuged at 4° C. and 8000 rpm for 10 minutes, washed twice with normal saline and centrifugated again. The obtained cells were disrupted, separated and purified, which was further stored at −20° C. The electrophoresis diagram of the obtain nitrilase mutant BrNIT$_{225-285}$ was as shown in FIG. 1.

3. Determine the Activity of Recombinant *Escherichia coli* Containing Nitrilase Mutant The activity of the recombinant *Escherichia coli* containing nitrilase mutant (E. coli BL21(DE3)/pET28b-BrNIT$_{0-85}$, E. coli BL21(DE3)/pET28b-BrNIT$_{85-175}$, E. coli BL21(DE3)/pET28b-BrNIT$_{175-225}$, E. coli BL21(DE3)/pET28b-BrNIT$_{225-285}$ and E. coli BL21(DE3)/pET28b-BrNIT$_{285-342}$) were determined. The reaction was performed in Tris-HCl buffer solution (50 mM, pH 8.0) containing nitrilase mutant (10 mL), racemic IBSN 30 g/L, wet cells 10 g/L at 30° C. and 200 rpm for 15 minutes. After reaction, 500 µL of reaction sample was taken and added with 200 µL 2 M HCl to end reaction.

The enantiomeric excess value of the substrate racemic IBSN and the product 3-cyano-5-Methylhexanoic acid was determined by gas chromatography. The gas chromatograph model was 7890N (Agilent) and the capillary column model was BGB-174 (BGB Analytik Switzerland). Chromatographic condition: injection volume was 1.0 µL, the temperatures of both the injection port and the detector were 250° C., the column temperature was 120° C. maintaining for 15 minutes, then the temperature was raised from 10° C./min to 170° C. and maintain for 9 minutes. The carrier gas was high-purity helium, the flow rate was 1.0 mL/min, the split ratio was 50:1.

The calculation of the enantiomeric excess value (ee) and the conversion rate (c) was referred to the calculation method of Rakels et al (Enzyme Microb. Technol., 1993, 15:1051).

The activities of the nitrilase mutants were as shown in Table 3:

TABLE 3

Activity determination results of the recombinant *escherichia coli* containing nitrilase mutant

| Strain | Relative activity (%) | E |
|---|---|---|
| E. coli BL21(DE3)/pET28b-BrNIT | 100 | 200 |
| E. coli BL21(DE3)/pET28b-BrNIT$_{0-85}$ | 112.4 | 300 |
| E. coli BL21(DE3)/pET28b-BrNIT$_{85-175}$ | 0 | ND |
| E. coli BL21(DE3)/pET28b-BrNIT$_{175-225}$ | 41.75 | 300 |
| E. coli BL21(DE3)/pET28b-BrNIT$_{225-285}$ | 249.5 | 500 |
| E. coli BL21(DE3)/pET28b-BrNIT$_{285-342}$ | 22.1 | 300 |

Note:
ND means No Detection.

4. Comparison of Nitrilase Mutant BrNIT$_{225-285}$ and Wild Type Nitrilase in Catalyzing Racemic IBSN Hydrolysis The recombinant E. coli BL21(DE3)/pET28b-BrNIT$_{225-285}$ obtained from culture and the recombinant E. coli BL21(DE3)/pET28b-BrNIT containing wild type nitrilase were taken as biocatalysts, compare the effect of their stereoselectivity in hydrolyzing racemic IBSN.

Figure 2:
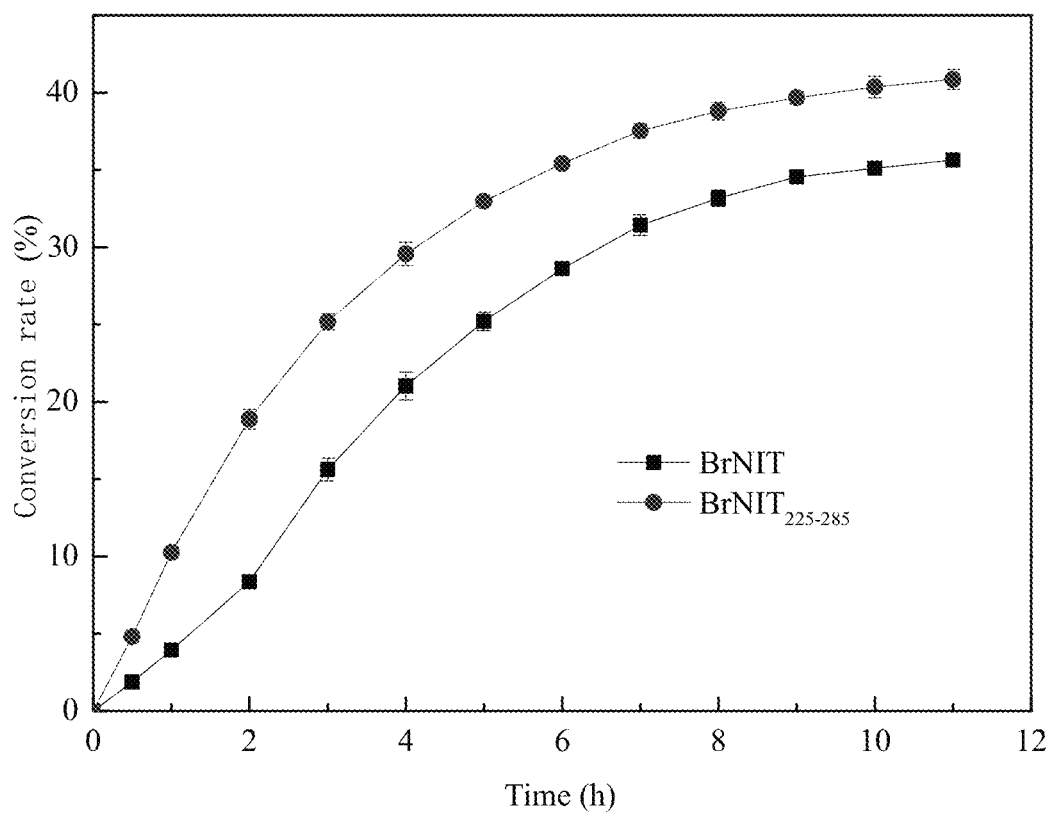
FIG. 2 is comparison of reaction progress of BrNIT mutant and the wild-type nitrilase for catalyzing 100 g/L racemic IBSN.

Reaction system composition (100 mL): Tris-HCl buffer solution (50 mM, pH 8.0), 1.5 g wet cell and 10 g racemic IBSN. The reaction was conducted at 35° C. and 200 rpm and 500 µL sampled was taken every 1 hours, which was further added with 200 µL 2 M HCl to stop the reaction. The progresses of the mutant and wild type nitrilase in catalyzing racemic IBSN hydrolysis were shown in FIG. 2.

5. Biosynthesis of (S)-3-Cyano-5-Methylhexanoic Acid with Recombinant E. coli BL21(DE3)/pET28b-BrNIT$_{225-285}$ The biosynthesis of (S)-3-cyano-5-methylhexanoic acid was performed in 100 mL Tris-HCl buffer solution (pH 8.0) with 2.0 g wet cells of recombinant E. coli BL21(DE3)/pET28b-BrNIT$_{225-285}$ (final concentration at 20 g/L) and 1 M racemic IBSN (136 g/L). The reaction was conducted at 30° C. and 200 rpm for 8 h, and during which, 500 µL sample was taken every 1 hours, which was further added with 200 µL 2 M HCl to stop the reaction. The sample test method was in reference to Step 3. The conversion rate reached 39.8%, and the ee value of the product (S)-3-cyano-5-methylhexanoic acid exceeded 99.3%. Compared with reported catalytic process, the additive amount of the cells was reduced by 2.5 times.

Embodiment 2

Construction of arabidopsis nitrilase mutant AtNIT$_{225-285}$ and its application in synthesizing (S)-3-cyano-5-methylhexanoic acid.

The amino acid sequence of the wild type arabidopsis nitrilase was SEQ ID No.9, which was encoded by the nucleotide sequence of SEQ ID No.10.

Arabidopsis nitrilase mutant AtNIT$_{225-285}$ was constructed in reference to Embodiment 1. The primers used for mutant construction were as shown in Table 4.

TABLE 4

AtNIT chimeric enzyme primer design table

| Primer designation | Primer sequence (5' to 3') |
|---|---|
| Peptide fragment forward primer (AaNIT) | CTAAAGAATGGCAGTCTTCTATGCTGCA CATCGC (SEQ ID NO: 31) |
| Peptide fragment reverse primer (AaNIT) | GATTCGAAGTTCGGACCAGCCAGAACCT GACCCAGC (SEQ ID NO: 32) |
| AtNIT cloning vectors forward primer | GCGATGTGCAGCATAGAAGACTGCCATT CTTTAG (SEQ ID NO: 33) |
| AtNIT cloning vectors reverse primer | GCTGGGTCAGGTTCTGGCTGGTCCGAAC TTCGAATC (SEQ ID NO: 34) |

The recombinant *E. coli* BL21(DE3)/pET28b-BrNIT$_{225-285}$ containing arabidopsis nitrilase mutant and the recombinant *E. coli* BL21(DE3)/pET28b-BrNIT containing wild type arabidopsis nitrilase were obtained in reference to Embodiment 1. After induced expression, whole cell was collected and disrupted, separated and purified, to obtain nitrilase mutant AtNIT$_{225-285}$. The electrophoresis diagram was shown in FIG. 1.

The reaction was performed in 10 mL Tris-HCl buffer solution (50 mM, pH 8.0) with 0.1 g (wet weight) resting cells containing arabidopsis nitrilase mutant and wild type nitrilase and 0.3 g racemic IBSN at 30° C. and 200 rpm. The activity of mutant AtNIT$_{225-285}$ in catalyzing racemic IBSN was 1.9 times of that of wild type nitrilase. After reaction for 24 hours, the conversion of IBSN by wild type AtNIT and mutant AtNIT$_{225-285}$ reached 25.64% and 48.76%, respectively, both of which the ee value exceeded 98.5%.

The invention claimed is:

1. A nitrilase mutant having the amino acid sequence of SEQ ID NO.1 or SEQ ID NO.3.

2. A coding gene for coding the nitrilase mutant according to claim 1, wherein the coding gene has the nucleotide sequence of SEQ ID NO.2 or SEQ ID NO.4.

3. A recombinant vector containing the coding gene according to claim 2.

4. A recombinant genetic engineering strain containing the recombinant vector according to claim 3.

5. A method for preparing the nitrilase mutant of claim 1, which is characterized in comprising the following steps:
　(1) based on turnip nitrilase gene or *arabidopsis* nitrilase gene sequence, designing a PCR primer by using *Arabis alpina* L, cDNA as a template, utilizing the primer to amplify to obtain a DNA fragment I or a DNA fragment II that contains nucleotide positions 673-855 of the *Arabis alpina* L, nitrilase nucleotide sequence (SEQ ID NO: 8);
　(2) taking a recombinant plasmid that carries turnip nitrilase gene or *arabidopsis* nitrilase gene sequence as a template, utilizing reverse PCR amplification to obtain a *Brassica rapa* nitrilase (BrNIT) plasmid fragment lack in nucleotide positions 676-858 of the turnip nitrilase nucleotide sequence (SEQ ID NO: 6) or obtain the *Arabidopsis thaliana* nitrilase (AtNIT) plasmid fragment lack in nucleotide positions 673-855 of the *arabidopsis* nitrilase nucleotide sequence (SEQ ID NO: 10);
　(3) recombining the DNA fragment I with the BrNIT plasmid fragment or recombining the DNA fragment II with the AtNIT plasmid fragment, and introducing the recombinant product into the host bacteria, filtering to obtain nitrilase mutant expression strain;
　(4) conducting induced expression to the nitrilase mutant expression strain to obtain the nitrilase mutant.

6. A method of using the nitrilase mutant of claim 1 in catalyzing racemic isobutylsuccinonitrile (IBSN) to prepare (S)-3-cyano-5-methylhexanoic acid, the method comprising the steps of:
　taking wet cells comprising a polynucleotide encoding the nitrilase mutant of claim 1, immobilized cells of the wet cells or pure enzyme extracted from ultrasonication of the wet cells as a catalyst,
　using racemic IBSN as a substrate, and
　using buffer solution of pH 5.0-10.0 as a reaction medium to conduct hydrolysis reaction at 25-45° C. and 100-300 rpm;
　after complete reaction, obtaining a mixture containing (S)-3-cyano-5-methylhexanoic acid, separating and purifying the mixture to obtain (S)-3-c5-methylhexanoic acid.

7. The method according to claim 6, which is characterized in that, in the reaction system, the final concentration of the substrate is 0.5-1.5 M, use amount of the catalyst is calculated based on weight of the wet cell at 10-30 g/L.

8. The method according to claim 6, which is characterized in that, reaction medium is Tris-HCl buffer solution with pH 8.0.

9. The method according to claim 6, which is characterized in that, the wet cells are recombinant *E. coli* BL21 (DE3)/pET28b-BrNIT$_{225-285}$ or *E. coli* BL21(DE3)/pET28b-AtNIT$_{225-285}$ containing nitrilase mutant coding gene; and wherein the method of fermental culture comprises: inoculating recombinant *E. coli* containing nitrilase mutant coding gene in a LB culture medium containing kanamycin and culturing until OD$_{600}$=0.6-0.8, adding isopropyl-β-D-thiogalactopyranoside of final concentration 0.1 mM, conducting induced culture at 28° C. for 10-12 hours, conducting centrifugation, collecting cells and obtaining the wet cell; wherein BrNIT represents *Brassica rapa* nitrilase and AtNIT represents *Arabidopsis thaliana* nitrilase.

\* \* \* \* \*

SEQUENCE LISTING

<160> NUMBER OF SEQ ID NOS: 34

<210> SEQ ID NO 1
<211> LENGTH: 350
<212> TYPE: PRT
<213> ORGANISM: Artificial sequence
<220> FEATURE:
<223> OTHER INFORMATION: Synthesized

<400> SEQUENCE: 1

```
Met Ser Gly Ser Glu Glu Met Ser Lys Ala Leu Asn Ala Thr Thr Pro
1               5                   10                  15

Gly Phe Pro Asp Ile Pro Ser Thr Ile Val Arg Ala Thr Ile Val Gln
            20                  25                  30

Ala Ser Thr Val Tyr Asn Asp Thr Pro Lys Thr Ile Glu Lys Ala Glu
        35                  40                  45

Lys Phe Ile Ala Glu Ala Ala Ser Asp Gly Ala Gln Leu Val Val Phe
    50                  55                  60

Pro Glu Ala Phe Ile Ala Gly Tyr Pro Arg Gly Tyr Arg Phe Gly Ile
65                  70                  75                  80

Gly Val Gly Val His Asn Glu Ala Gly Arg Asp Cys Phe Arg Arg Tyr
                85                  90                  95

His Ala Ser Ala Ile Val Val Pro Gly Pro Glu Val Asp Lys Leu Ala
            100                 105                 110

Glu Ile Ala Arg Lys Tyr Lys Val Tyr Leu Val Met Gly Ala Met Glu
        115                 120                 125

Lys Asp Gly Tyr Thr Leu Tyr Cys Thr Ala Leu Phe Phe Ser Ser Glu
    130                 135                 140

Gly Arg Phe Leu Gly Lys His Arg Lys Val Met Pro Thr Ser Leu Glu
145                 150                 155                 160

Arg Cys Ile Trp Gly Phe Gly Asp Gly Ser Thr Ile Pro Val Tyr Asp
                165                 170                 175

Thr Pro Leu Gly Lys Leu Gly Ala Ala Ile Cys Trp Glu Asn Arg Met
            180                 185                 190

Pro Leu Tyr Arg Thr Ser Leu Tyr Gly Lys Gly Ile Glu Leu Tyr Cys
        195                 200                 205

Ala Pro Thr Ala Asp Gly Ser Lys Glu Trp Gln Ser Ser Met Leu His
    210                 215                 220
```

```
Ile Ala Leu Glu Gly Gly Cys Phe Val Leu Ser Ala Cys Gln Phe Cys
225                 230                 235                 240

Arg Arg Lys Asp Phe Pro Asp His Pro Asp Tyr Leu Phe Thr Asp Trp
                245                 250                 255

Asp Asp Asn Gln Glu Asp His Ala Ile Val Ser Gln Gly Gly Ser Val
            260                 265                 270

Ile Ile Ser Pro Leu Gly Gln Val Leu Ala Gly Pro Asn Phe Glu Ser
        275                 280                 285

Glu Gly Leu Ile Thr Ala Asp Leu Asp Leu Gly Asp Val Ala Arg Ala
    290                 295                 300

Lys Leu Tyr Phe Asp Val Val Gly His Tyr Ser Arg Pro Glu Ile Phe
305                 310                 315                 320

Asn Leu Thr Val Asn Glu Thr Pro Lys Lys Pro Val Thr Phe Val Ser
                325                 330                 335

Lys Ser Val Lys Ala Glu Asp Asp Ser Glu Pro Gln Asp Lys
            340                 345                 350
```

```
<210> SEQ ID NO 2
<211> LENGTH: 1050
<212> TYPE: DNA
<213> ORGANISM: Artificial sequence
<220> FEATURE:
<223> OTHER INFORMATION: Synthesized

<400> SEQUENCE: 2
atgtctggct ctgaagaaat gtccaaagct ctgaatgcta ccactccagg tttcccggac    60
atccctagca ccatcgttcg cgccacgatc gttcaggctt ccactgtata acgacact     120
cctaaaacca tcgaaaaagc tgaaaaattc atcgcggaag ctgctagcga cggtgcgcag   180
ctggtggtct ttccggaagc tttcatcgct ggttacccgc gtggctatcg tttcggcatc   240
ggtgtaggtg tgcacaacga ggcgggccgt gattgtttcc gccgctatca tgctagcgcg   300
atcgttgtcc cgggtccgga ggttgataaa ctggcagaaa ttgctcgtaa atacaaagtc   360
tacctggtaa tgggtgccat ggagaaagat ggttataccc tgtactgtac tgcgctgttt   420
ttcagctctg aaggtcgttt cctgggcaag caccgcaaag tcatgccgac gtctctggaa   480
cgttgcatct ggggcttcgg tgatggttct actatcccgg tctacgacac cccgctgggc   540
aagctgggcg ccgcaatctg ttgggaaaac cgcatgccgc tgtaccgtac tagcctgtac   600
ggcaaaggta tcgagctgta ttgcgctccg actgccgatg gctctaaaga atggcagtct   660
tctatgctgc acatcgctct ggaaggtggt tgcttcgttc tgtctgcttg ccagttctgc   720
cgtcgtaaag acttcccgga ccacccggac tacctgttca ccgactggga cgacaaccag   780
gaagaccacg ctatcgtttc tcagggtggt tctgttatca tctctccgct gggtcaggtt   840
ctggctggtc cgaacttcga gtctgagggc ctgatcactg cagatctgga tctgggcgat   900
gtagcgcgtg caaaactgta tttcgatgtt gttggtcact actccgccc tgagattttt   960
aatctgacgg ttaacgagac tccgaagaaa ccggttactt cgtttccaa gtccgtaaaa   1020
gctgaggacg actctgagcc gcaggacaaa                                     1050
```

```
<210> SEQ ID NO 3
<211> LENGTH: 351
<212> TYPE: PRT
<213> ORGANISM: Artificial sequence
<220> FEATURE:
<223> OTHER INFORMATION: Synthesized

<400> SEQUENCE: 3
```

```
Met Ser Ser Thr Lys Asp Met Ser Thr Val Gln Asn Ala Thr Pro Phe
1               5                   10                  15

Asn Gly Val Ala Pro Ser Thr Val Arg Val Thr Ile Val Gln Ser
            20                  25                  30

Ser Thr Val Tyr Asn Asp Thr Pro Ala Thr Ile Asp Lys Ala Glu Lys
            35                  40                  45

Tyr Ile Val Glu Ala Ala Ser Lys Gly Ala Glu Leu Val Leu Phe Pro
50                  55                  60

Glu Gly Phe Ile Gly Gly Tyr Pro Arg Gly Phe Arg Phe Gly Leu Ala
65              70                  75                  80

Val Gly Val His Asn Glu Glu Gly Arg Asp Glu Phe Arg Lys Tyr His
                85                  90                  95

Ala Ser Ala Ile His Val Pro Gly Pro Glu Val Ala Arg Leu Ala Asp
            100                 105                 110

Val Ala Arg Lys Asn His Val Tyr Leu Val Met Gly Ala Ile Glu Lys
            115                 120                 125

Glu Gly Tyr Thr Leu Tyr Cys Thr Val Leu Phe Phe Ser Pro Gln Gly
    130                 135                 140

Gln Phe Leu Gly Lys His Arg Lys Leu Met Pro Thr Ser Leu Glu Arg
145                 150                 155                 160

Cys Ile Trp Gly Gln Gly Asp Gly Ser Thr Ile Pro Val Tyr Asp Thr
                165                 170                 175

Pro Ile Gly Lys Leu Gly Ala Ala Ile Cys Trp Glu Asn Arg Met Pro
            180                 185                 190

Leu Tyr Arg Thr Ala Leu Tyr Ala Lys Gly Ile Glu Leu Tyr Cys Ala
            195                 200                 205

Pro Thr Ala Asp Gly Ser Lys Glu Trp Gln Ser Ser Met Leu His Ile
210                 215                 220

Ala Leu Glu Gly Gly Cys Phe Val Leu Ser Ala Cys Gln Phe Cys Arg
225                 230                 235                 240

Arg Lys Asp Phe Pro Asp His Pro Asp Tyr Leu Phe Thr Asp Trp Asp
                245                 250                 255

Asp Asn Gln Glu Asp His Ala Ile Val Ser Gln Gly Gly Ser Val Ile
            260                 265                 270

Ile Ser Pro Leu Gly Gln Val Leu Ala Gly Pro Asn Phe Glu Ser Glu
    275                 280                 285

Gly Leu Val Thr Ala Asp Ile Asp Leu Gly Asp Ile Ala Arg Ala Lys
290                 295                 300

Leu Tyr Phe Asp Ser Val Gly His Tyr Ser Arg Pro Asp Val Leu His
305                 310                 315                 320

Leu Thr Val Asn Glu His Pro Arg Lys Ser Val Thr Phe Val Thr Lys
                325                 330                 335

Val Glu Lys Ala Glu Asp Asp Ser Asn Lys Tyr Lys Leu Ala Ala
            340                 345                 350
```

<210> SEQ ID NO 4
<211> LENGTH: 1053
<212> TYPE: DNA
<213> ORGANISM: Artificial sequence
<220> FEATURE:
<223> OTHER INFORMATION: Synthesized

<400> SEQUENCE: 4
atgagctcta ctaaagatat gtccacggtt caaaacgcaa ctccttcaa cggcgtcgca    60

```
ccgtccacta ctgttcgcgt tactattgta cagagcagca ccgtgtataa tgacacgcca    120
gcaaccatcg ataaagcaga aaatacatc gtggaagcgg catccaaagg tgcggaactg     180
gtcctgttcc cagaaggctt tattggtggt tatccgcgtg gtttccgttt cggcctggct    240
gttggtgtgc ataacgaaga aggtcgtgac gagttccgta ataccacgc tccgcaatc      300 cacgtgccgg gtccggaagt agctcgcctg gcagacgttg cacgtaagaa ccatgtatac    360
ctggttatgg gcgcgattga aaaggaaggt tatactctgt attgcaccgt actgttcttc    420
tctccgcaag gccagttcct gggcaagcac cgtaagctga tgccaacgtc cctggaacgt    480
tgtatctggg gccagggtga tggttctacc atcccggttt atgataccc gatcggtaaa     540 ctgggtgcgg ccatctgttg ggaaaaccgt atgcctctgt accgtaccgc cctgtatgcg    600
aaaggtattg agctgtattg cgcccctacc gccgacggct ctaaagaatg cagtcttct     660 atgctgcaca tcgctctgga aggtggttgc ttcgttctgt ctgcttgcca gttctgccgt    720
cgtaaagact tcccggacca cccggactac ctgttcaccg actgggacga caaccaggaa    780
gaccacgcta tcgtttctca gggtggttct gttatcatct ctccgctggg tcaggttctg    840
gctggtccga acttcgaatc tgagggtctg gtcactgcag acatcgacct gggcgatatc    900
gctcgtgcta aactgtactt cgactctgtt ggccactact cccgtccaga tgtgctgcac    960
ctgaccgtaa acgaacaccc gcgtaaatcc gtcacttttg tgaccaaagt ggaaaaagct   1020
gaagatgact ctaacaaata caagcttgcg gcc                                1053
```

<210> SEQ ID NO 5
<211> LENGTH: 350
<212> TYPE: PRT
<213> ORGANISM: Brassica rapa

<400> SEQUENCE: 5

```
Met Ser Gly Ser Glu Glu Met Ser Lys Ala Leu Asn Ala Thr Thr Pro
1               5                   10                  15

Gly Phe Pro Asp Ile Pro Ser Thr Ile Val Arg Ala Thr Ile Val Gln
            20                  25                  30

Ala Ser Thr Val Tyr Asn Asp Thr Pro Lys Thr Ile Glu Lys Ala Glu
        35                  40                  45

Lys Phe Ile Ala Glu Ala Ala Ser Asp Gly Ala Gln Leu Val Val Phe
    50                  55                  60

Pro Glu Ala Phe Ile Ala Gly Tyr Pro Arg Gly Tyr Arg Phe Gly Ile
65                  70                  75                  80

Gly Val Gly Val His Asn Glu Ala Gly Arg Asp Cys Phe Arg Arg Tyr
                85                  90                  95

His Ala Ser Ala Ile Val Val Pro Gly Pro Glu Val Asp Lys Leu Ala
            100                 105                 110

Glu Ile Ala Arg Lys Tyr Lys Val Tyr Leu Val Met Gly Ala Met Glu
        115                 120                 125

Lys Asp Gly Tyr Thr Leu Tyr Cys Thr Ala Leu Phe Phe Ser Ser Glu
    130                 135                 140

Gly Arg Phe Leu Gly Lys His Arg Lys Val Met Pro Thr Ser Leu Glu
145                 150                 155                 160

Arg Cys Ile Trp Gly Phe Gly Asp Gly Ser Thr Ile Pro Val Tyr Asp
                165                 170                 175

Thr Pro Leu Gly Lys Leu Gly Ala Ala Ile Cys Trp Glu Asn Arg Met
            180                 185                 190

Pro Leu Tyr Arg Thr Ser Leu Tyr Gly Lys Gly Ile Glu Leu Tyr Cys
```

```
                195                 200                 205
Ala Pro Thr Ala Asp Gly Ser Lys Glu Trp Gln Ser Ser Met Met His
    210                 215                 220

Ile Ala Ile Glu Gly Gly Cys Phe Val Leu Ser Ala Cys Gln Phe Cys
225                 230                 235                 240

Leu Arg Lys Asp Phe Pro Asp His Ala Asp Tyr Leu Phe Thr Asp Trp
                245                 250                 255

Tyr Pro Asp Gln His Gln Glu Ala Ile Val Ser Gln Gly Gly Ser Val
            260                 265                 270

Ile Ile Ser Pro Leu Gly Lys Ile Leu Ala Gly Pro Asn Phe Glu Ser
        275                 280                 285

Glu Gly Leu Ile Thr Ala Asp Leu Asp Leu Gly Asp Val Ala Arg Ala
    290                 295                 300

Lys Leu Tyr Phe Asp Val Val Gly His Tyr Ser Arg Pro Glu Ile Phe
305                 310                 315                 320

Asn Leu Thr Val Asn Glu Thr Pro Lys Lys Pro Val Thr Phe Val Ser
                325                 330                 335

Lys Ser Val Lys Ala Glu Asp Asp Ser Glu Pro Gln Asp Lys
            340                 345                 350

<210> SEQ ID NO 6
<211> LENGTH: 1050
<212> TYPE: DNA
<213> ORGANISM: Brassica rapa

<400> SEQUENCE: 6
atgtctggct ctgaagaaat gtccaaagct ctgaatgcta ccactccagg tttcccggac        60
atccctagca ccatcgttcg cgccacgatc gttcaggctt ccactgtata caacgacact       120
cctaaaacca tcgaaaaagc tgaaaaattc atcgcggaag ctgctagcga cggtgcgcag       180
ctggtggtct ttccggaagc tttcatcgct ggttacccgc gtggctatcg tttcggcatc       240
ggtgtaggtg tgcacaacga ggcgggccgt gattgtttcc gccgctatca tgctagcgcg       300
atcgttgtcc gggtccggag ggttgataaa ctggcagaaa ttgctcgtaa atacaaagtc       360
tacctggtaa tgggtgccat ggagaaagat ggttataccc tgtactgtac tgcgctgttt       420
ttcagctctg aaggtcgttt cctgggcaag caccgcaaag tcatgccgac gtctctggaa       480
cgttgcatct ggggcttcgg tgatggttct actatcccgg tctacgacac cccgctgggc       540
aagctgggcg ccgcaatctg ttgggaaaac cgcatgccgc tgtaccgtac tagcctgtac       600
ggcaaaggta tcgagctgta ttgcgctccg actgccgatg ctctaaaga atggcagtcc       660 tccatgatgc acatcgctat cgaaggcggt tgtttcgttc tgtctgcttg ccaattctgc       720
ctgcgcaaag acttcccgga ccacgctgac tatctgttta ccgattggta cccggatcag       780
caccaggaag cgattgtaag ccagggtggt tctgttatca ttagcccact gggtaaaatc       840
ctggcgggtc cgaacttcga gtctgagggc ctgatcactg cagatctgga tctgggcgat       900
gtagcgcgtg caaaactgta tttcgatgtt gttggtcact actcccgccc tgagattttt       960
aatctgacgg ttaacgagac tccgaagaaa ccggttactt tcgtttccaa gtccgtaaaa      1020
gctgaggacg actctgagcc gcaggacaaa                                        1050

<210> SEQ ID NO 7
<211> LENGTH: 346
<212> TYPE: PRT
<213> ORGANISM: Arabis alpine
```

<400> SEQUENCE: 7

Met Ser Gly Lys Glu Glu Met Ser Ser Val Lys Asn Thr Thr Pro Ala
1               5                   10                  15

Asn Gly Val Ala Pro Ser Ser Ile Val Arg Ala Ser Ile Val Gln Ala
            20                  25                  30

Ser Thr Val Tyr Asn Asn Thr Pro Ala Thr Leu Glu Lys Ala Glu Lys
        35                  40                  45

Leu Ile Ala Glu Ala Ala Ser Asn Gly Ser Lys Leu Val Val Phe Pro
    50                  55                  60

Glu Ala Phe Ile Gly Gly Tyr Pro Arg Gly Phe Arg Phe Gly Ile Gly
65              70                  75                  80

Val Gly Val His Asn Glu Asp Gly Arg Asp Glu Phe Arg Asn Tyr His
            85                  90                  95

Ala Ser Ala Ile Arg Val Pro Gly Pro Glu Val Glu Lys Leu Ala Glu
            100                 105                 110

Val Ala Gly Lys Asn Asn Val Tyr Leu Val Met Gly Ala Ile Glu Lys
        115                 120                 125

Asp Gly Tyr Thr Leu Tyr Cys Thr Ala Leu Phe Phe Ser Ser Gln Gly
    130                 135                 140

Leu Phe Leu Gly Lys His Arg Lys Leu Met Pro Thr Ser Leu Glu Arg
145                 150                 155                 160

Cys Ile Trp Gly Tyr Gly Asp Gly Ser Thr Ile Pro Val Tyr Asp Thr
            165                 170                 175

Pro His Gly Lys Leu Gly Ala Ala Ile Cys Trp Glu Asn Arg Met Pro
        180                 185                 190

Leu Tyr Arg Thr Ala Leu Tyr Ala Lys Gly Val Glu Ile Tyr Cys Ala
    195                 200                 205

Pro Thr Ala Asp Gly Ser Lys Glu Trp Gln Ser Ser Met Leu His Ile
210                 215                 220

Ala Leu Glu Gly Gly Cys Phe Val Leu Ser Ala Cys Gln Phe Cys Arg
225                 230                 235                 240

Arg Lys Asp Phe Pro Asp His Pro Asp Tyr Leu Phe Thr Asp Trp Asp
            245                 250                 255

Asp Asn Gln Glu Asp His Ala Ile Val Ser Gln Gly Gly Ser Val Ile
        260                 265                 270

Ile Ser Pro Leu Gly Gln Val Leu Ala Gly Pro Asn Phe Glu Ser Glu
    275                 280                 285

Gly Leu Val Thr Ala Asp Leu Asp Leu Gly Asp Val Ala Arg Ala Lys
290                 295                 300

Leu Tyr Phe Asp Val Val Gly His Tyr Ser Lys Pro Glu Val Phe Asn
305                 310                 315                 320

Leu Thr Val Asn Glu Asp Arg Lys Lys Pro Val Thr Phe Val Ser Lys
            325                 330                 335

Val Glu Lys Ala Glu Asp Glu Pro Lys Lys
            340                 345

<210> SEQ ID NO 8
<211> LENGTH: 1038
<212> TYPE: DNA
<213> ORGANISM: Arabis alpine

<400> SEQUENCE: 8
atgtctggta aagaagaaat gtcttctgtt aaaaacacca ccccggctaa cggtgttgct     60
ccgtcttcta tcgttcgtgc ttctatcgtt caggcttcta ccgtttacaa caacaccccg    120

```
gctaccctgg aaaaagctga aaaactgatc gctgaagctg cttctaacgg ttcgaagctg      180
gttgtattcc cggaagcgtt catcggcggt tacccacgtg gctttaggtt cggtataggt      240
gttggtgttc acaacgaaga cggtcgtgac gaattccgta actaccacgc ttctgctatc      300
cgtgttccgg gtccggaagt tgaaaaactg gctgaagttg ctggtaaaaa caacgtttac      360
ctggttatgg gtgctatcga aaaagacggt tacaccctgt actgcaccgc tctgttcttc      420
tcttctcagg gtctgttcct gggtaaacac cgtaaactga tgccgacctc tctggaacgt      480
tgcatctggg gttacggtga cggttcgact atcccggtgt acgacacacc gcacggtaaa      540
ctgggtgctg ctatctgctg ggaaaaccgt atgccgctgt accgtaccgc tctgtacgct      600
aaaggtgttg aaatctactg cgctccgacc gctgacggtt ctaaagaatg cagtcttct       660 atgctgcaca tcgctctgga aggtggttgc ttcgttctgt ctgcttgcca gttctgccgt      720
cgtaaagact tcccggacca cccggactac ctgttcaccg actgggacga caaccaggaa      780
gaccacgcta tcgtttctca gggtggttct gttatcatct ctccgctggg tcaggttctg      840
gctggtccga acttcgaatc tgaaggtctg gttaccgctg acctggacct gggtgacgtt      900
gctcgtgcta aactgtactt cgacgttgtt ggtcactact ctaaaccgga agttttcaac      960
ctgaccgtta acgaagaccg taaaaaaccg gttaccttcg tttctaaagt tgaaaaagct     1020
gaagacgaac cgaaaaaa                                                  1038
```

<210> SEQ ID NO 9
<211> LENGTH: 351
<212> TYPE: PRT
<213> ORGANISM: Arabidopsis thaliana

<400> SEQUENCE: 9

```
Met Ser Ser Thr Lys Asp Met Ser Thr Val Gln Asn Ala Thr Pro Phe
1               5                   10                  15

Asn Gly Val Ala Pro Ser Thr Thr Val Arg Val Thr Ile Val Gln Ser
            20                  25                  30

Ser Thr Val Tyr Asn Asp Thr Pro Ala Thr Ile Asp Lys Ala Glu Lys
        35                  40                  45

Tyr Ile Val Glu Ala Ala Ser Lys Gly Ala Glu Leu Val Leu Phe Pro
    50                  55                  60

Glu Gly Phe Ile Gly Gly Tyr Pro Arg Gly Phe Arg Phe Gly Leu Ala
65                  70                  75                  80

Val Gly Val His Asn Glu Glu Gly Arg Asp Glu Phe Arg Lys Tyr His
                85                  90                  95

Ala Ser Ala Ile His Val Pro Gly Pro Glu Val Ala Arg Leu Ala Asp
            100                 105                 110

Val Ala Arg Lys Asn His Val Tyr Leu Val Met Gly Ala Ile Glu Lys
        115                 120                 125

Glu Gly Tyr Thr Leu Tyr Cys Thr Val Leu Phe Phe Ser Pro Gln Gly
    130                 135                 140

Gln Phe Leu Gly Lys His Arg Lys Leu Met Pro Thr Ser Leu Glu Arg
145                 150                 155                 160

Cys Ile Trp Gly Gln Gly Asp Gly Ser Thr Ile Pro Val Tyr Asp Thr
                165                 170                 175

Pro Ile Gly Lys Leu Gly Ala Ala Ile Cys Trp Glu Asn Arg Met Pro
            180                 185                 190

Leu Tyr Arg Thr Ala Leu Tyr Ala Lys Gly Ile Glu Leu Tyr Cys Ala
        195                 200                 205
```

```
Pro Thr Ala Asp Gly Ser Lys Glu Trp Gln Ser Ser Met Leu His Ile
    210                 215                 220
Ala Ile Glu Gly Gly Cys Phe Val Leu Ser Ala Cys Gln Phe Cys Gln
225                 230                 235                 240
Arg Lys His Phe Pro Asp His Pro Asp Tyr Leu Phe Thr Asp Trp Tyr
                245                 250                 255
Asp Asp Lys Glu His Asp Ser Ile Val Ser Gln Gly Gly Ser Val Ile
                260                 265                 270
Ile Ser Pro Leu Gly Gln Val Leu Ala Gly Pro Asn Phe Glu Ser Glu
            275                 280                 285
Gly Leu Val Thr Ala Asp Ile Asp Leu Gly Asp Ile Ala Arg Ala Lys
    290                 295                 300
Leu Tyr Phe Asp Ser Val Gly His Tyr Ser Arg Pro Asp Val Leu His
305                 310                 315                 320
Leu Thr Val Asn Glu His Pro Arg Lys Ser Val Thr Phe Val Thr Lys
                325                 330                 335
Val Glu Lys Ala Glu Asp Asp Ser Asn Lys Tyr Lys Leu Ala Ala
                340                 345                 350

<210> SEQ ID NO 10
<211> LENGTH: 1053
<212> TYPE: DNA
<213> ORGANISM: Arabidopsis thaliana

<400> SEQUENCE: 10
atgagctcta ctaaagatat gtccacggtt caaaacgcaa ctcctttcaa cggcgtcgca      60
ccgtccacta ctgttcgcgt tactattgta cagagcagca ccgtgtataa tgacacgcca     120
gcaaccatcg ataaagcaga aaatacatc gtggaagcgg catccaaagg tgcggaactg      180
gtcctgttcc cagaaggctt tattggtggt tatccgcgtg gtttccgttt cggcctggct     240
gttggtgtgc ataacgaaga aggtcgtgac gagttccgta ataccacgc tccgcaatc      300 cacgtgccgg gtccggaagt agctcgcctg gcagacgttg cacgtaagaa ccatgtatac     360
ctggttatgg gcgcgattga aaaggaaggt tatactctgt attgcaccgt actgttcttc     420
tctccgcaag gccagttcct gggcaagcac cgtaagctga tgccaacgtc cctggaacgt     480
tgtatctggg gccagggtga tggttctacc atcccggttt atgataccc gatcggtaaa     540 ctgggtgcgg ccatctgttg gaaaaaccgt atgcctctgt accgtaccgc cctgtatgcg     600
aaaggtattg agctgtattg cgcccctacc gccgacggct ctaaagagtg gcagtcctcc     660
atgctgcaca tcgcgattga gggtggctgc ttcgtgctgt ctgcctgcca gttttgccag     720 cgtaaaacact ttccggacca tccggactat ctgttcacgg attggtacga tgacaaagaa     780
cacgacagca tcgtttccca gggtggttct gttatcatta gcccgctggg ccaggtactg     840
gctggtccga acttcgaatc tgagggtctg gtcactgcag acatcgacct gggcgatatc     900
gctcgtgcta aactgtactt cgactctgtt ggccactact cccgtccaga tgtgctgcac     960
ctgaccgtaa acgaacaccc gcgtaaatcc gtcacttttg tgaccaaagt ggaaaaagct    1020
gaagatgact ctaacaaata caagcttgcg gcc                                 1053

<210> SEQ ID NO 11
<211> LENGTH: 25
<212> TYPE: DNA
<213> ORGANISM: Artificial sequence
<220> FEATURE:
<223> OTHER INFORMATION: Synthesized
```

<400> SEQUENCE: 11
ccatgtctgg taaagaagaa atgtc                                          25

<210> SEQ ID NO 12
<211> LENGTH: 26
<212> TYPE: DNA
<213> ORGANISM: Artificial sequence
<220> FEATURE:
<223> OTHER INFORMATION: Synthesized

<400> SEQUENCE: 12
cgttgtgaac accaacacct ataccg                                         26

<210> SEQ ID NO 13
<211> LENGTH: 34
<212> TYPE: DNA
<213> ORGANISM: Artificial sequence
<220> FEATURE:
<223> OTHER INFORMATION: Synthesized

<400> SEQUENCE: 13
gacatttctt ctttaccaga catggtatat ctcc                                34

<210> SEQ ID NO 14
<211> LENGTH: 26
<212> TYPE: DNA
<213> ORGANISM: Artificial sequence
<220> FEATURE:
<223> OTHER INFORMATION: Synthesized

<400> SEQUENCE: 14
cggtataggt gttggtgttc acaacg                                         26

<210> SEQ ID NO 15
<211> LENGTH: 38
<212> TYPE: DNA
<213> ORGANISM: Artificial sequence
<220> FEATURE:
<223> OTHER INFORMATION: Synthesized

<400> SEQUENCE: 15
gtgtaggtgt gcacaacgaa gacggtcgtg acgaattc                            38

<210> SEQ ID NO 16
<211> LENGTH: 38
<212> TYPE: DNA
<213> ORGANISM: Artificial sequence
<220> FEATURE:
<223> OTHER INFORMATION: Synthesized

<400> SEQUENCE: 16
gtcgaaccgt caccgtaacc ccagatgcaa cgttccag                            38

<210> SEQ ID NO 17
<211> LENGTH: 38
<212> TYPE: DNA
<213> ORGANISM: Artificial sequence
<220> FEATURE:
<223> OTHER INFORMATION: Synthesized

<400> SEQUENCE: 17
gaattcgtca cgaccgtctt cgttgtgcac acctacac                            38

<210> SEQ ID NO 18

<210> SEQ ID NO 18
<211> LENGTH: 38
<212> TYPE: DNA
<213> ORGANISM: Artificial sequence
<220> FEATURE:
<223> OTHER INFORMATION: Synthesized

<400> SEQUENCE: 18
ctggaacgtt gcatctgggg ttacggtgac ggttcgac            38

<210> SEQ ID NO 19
<211> LENGTH: 30
<212> TYPE: DNA
<213> ORGANISM: Artificial sequence
<220> FEATURE:
<223> OTHER INFORMATION: Synthesized

<400> SEQUENCE: 19
ggtgacggtt cgactatccc ggtgtacgac            30

<210> SEQ ID NO 20
<211> LENGTH: 29
<212> TYPE: DNA
<213> ORGANISM: Artificial sequence
<220> FEATURE:
<223> OTHER INFORMATION: Synthesized

<400> SEQUENCE: 20
gcgatgtgca gcatagaaga ctgccattc            29

<210> SEQ ID NO 21
<211> LENGTH: 30
<212> TYPE: DNA
<213> ORGANISM: Artificial sequence
<220> FEATURE:
<223> OTHER INFORMATION: Synthesized

<400> SEQUENCE: 21
gtcgtacacc gggatagtcg aaccgtcacc            30

<210> SEQ ID NO 22
<211> LENGTH: 29
<212> TYPE: DNA
<213> ORGANISM: Artificial sequence
<220> FEATURE:
<223> OTHER INFORMATION: Synthesized

<400> SEQUENCE: 22
gaatggcagt cttctatgct gcacatcgc            29

<210> SEQ ID NO 23
<211> LENGTH: 29
<212> TYPE: DNA
<213> ORGANISM: Artificial sequence
<220> FEATURE:
<223> OTHER INFORMATION: Synthesized

<400> SEQUENCE: 23
gaatggcagt cttctatgct gcacatcgc            29

<210> SEQ ID NO 24
<211> LENGTH: 28
<212> TYPE: DNA
<213> ORGANISM: Artificial sequence
<220> FEATURE:
<223> OTHER INFORMATION: Synthesized

<400> SEQUENCE: 24
gaagttcgga ccagccagaa cctgaccc                                    28

<210> SEQ ID NO 25
<211> LENGTH: 29
<212> TYPE: DNA
<213> ORGANISM: Artificial sequence
<220> FEATURE:
<223> OTHER INFORMATION: Synthesized

<400> SEQUENCE: 25
gcgatgtgca gcatagaaga ctgccattc                                   29

<210> SEQ ID NO 26
<211> LENGTH: 28
<212> TYPE: DNA
<213> ORGANISM: Artificial sequence
<220> FEATURE:
<223> OTHER INFORMATION: Synthesized

<400> SEQUENCE: 26
gggtcaggtt ctggctggtc cgaacttc                                    28

<210> SEQ ID NO 27
<211> LENGTH: 32
<212> TYPE: DNA
<213> ORGANISM: Artificial sequence
<220> FEATURE:
<223> OTHER INFORMATION: Synthesized

<400> SEQUENCE: 27
ggtaaaatcc tgcgggtcc gaacttcgaa tc                                32

<210> SEQ ID NO 28
<211> LENGTH: 33
<212> TYPE: DNA
<213> ORGANISM: Artificial sequence
<220> FEATURE:
<223> OTHER INFORMATION: Synthesized

<400> SEQUENCE: 28
gtggtggtgg tggtgctcga gtcttttttt cgg                              33

<210> SEQ ID NO 29
<211> LENGTH: 32
<212> TYPE: DNA
<213> ORGANISM: Artificial sequence
<220> FEATURE:
<223> OTHER INFORMATION: Synthesized

<400> SEQUENCE: 29
gattcgaagt tcggacccgc caggatttta cc                               32

<210> SEQ ID NO 30
<211> LENGTH: 33
<212> TYPE: DNA
<213> ORGANISM: Artificial sequence
<220> FEATURE:
<223> OTHER INFORMATION: Synthesized

<400> SEQUENCE: 30
ccgaaaaaaa gactcgagca ccaccaccac cac                              33

<210> SEQ ID NO 31
<211> LENGTH: 34
<212> TYPE: DNA

```
<213> ORGANISM: Artificial sequence
<220> FEATURE:
<223> OTHER INFORMATION: Synthesized

<400> SEQUENCE: 31
ctaaagaatg gcagtcttct atgctgcaca tcgc                                    34

<210> SEQ ID NO 32
<211> LENGTH: 36
<212> TYPE: DNA
<213> ORGANISM: Artificial sequence
<220> FEATURE:
<223> OTHER INFORMATION: Synthesized

<400> SEQUENCE: 32
gattcgaagt tcggaccagc cagaacctga cccagc                                  36

<210> SEQ ID NO 33
<211> LENGTH: 34
<212> TYPE: DNA
<213> ORGANISM: Artificial sequence
<220> FEATURE:
<223> OTHER INFORMATION: Synthesized

<400> SEQUENCE: 33
gcgatgtgca gcatagaaga ctgccattct ttag                                    34

<210> SEQ ID NO 34
<211> LENGTH: 36
<212> TYPE: DNA
<213> ORGANISM: Artificial sequence
<220> FEATURE:
<223> OTHER INFORMATION: Synthesized

<400> SEQUENCE: 34
gctgggtcag gttctggctg gtccgaactt cgaatc                                  36
```